US007761309B2

(12) United States Patent
Sacco et al.

(10) Patent No.: US 7,761,309 B2
(45) Date of Patent: Jul. 20, 2010

(54) METHOD AND SYSTEM OF MASS AND MULTIPLE CASUALTY TRIAGE

(75) Inventors: William J. Sacco, Bel Air, MD (US); D. Michael Navin, Bel Air, MD (US)

(73) Assignee: ThinkSharp, Inc., Bel Air, MD (US)

( * ) Notice: Subject to any disclaimer, the term of this patent is extended or adjusted under 35 U.S.C. 154(b) by 1501 days.

(21) Appl. No.: 10/385,829

(22) Filed: Mar. 11, 2003

(65) Prior Publication Data

US 2004/0078223 A1 Apr. 22, 2004

Related U.S. Application Data

(60) Provisional application No. 60/367,527, filed on Mar. 22, 2002, provisional application No. 60/406,225, filed on Aug. 25, 2002.

(51) Int. Cl.
*G06Q 10/00* (2006.01)
*G06Q 50/00* (2006.01)
(52) U.S. Cl. .................. 705/2; 705/3; 705/4; 235/385
(58) Field of Classification Search .................. 235/385
See application file for complete search history.

(56) References Cited

U.S. PATENT DOCUMENTS

| | | | |
|---|---|---|---|
| 5,809,477 A | 9/1998 | Pollack | |
| 5,964,065 A | 10/1999 | Migurski et al. | ............... 52/64 |
| 6,305,605 B1 | 10/2001 | Goetz et al. | ................. 235/385 |
| 6,383,135 B1 | 5/2002 | Chikovani et al. | ........... 600/300 |
| 6,416,480 B1 | 7/2002 | Nenov | ........................ 600/557 |

(Continued)

FOREIGN PATENT DOCUMENTS

JP 10-116023 6/1998

(Continued)

OTHER PUBLICATIONS

Weiser, Benjamin. "Medicine's Reliability Rivaled by Software." The Washington Post. Washington DC: Jan. 1, 1992, p. a. 08.*

(Continued)

*Primary Examiner*—Gerald J. O'Connor
*Assistant Examiner*—Linh Michelle Le
(74) *Attorney, Agent, or Firm*—Blank Rome LLP (57) ABSTRACT

The present invention is a method and system of triage that assesses a severity score for each casualty, and determines a treatment prioritization plan to maximize the number of survivors. The present invention includes a score-based mathematical algorithm for resource-constrained triage, where an optimal number of survivors is determined through a methodology that can be mathematically modeled and solved, a methodology that considers victim survival probabilities, victim deterioration rates, and resource availability. First, each casualty is assessed and an RPM severity score is assigned based upon a sum of coded values for respiratory rate, pulse rate, and best motor response. Next, treatment priorities are determined from analytical or mathematical techniques, such as dynamic or linear programming, in consideration of survival probabilities associated with each RPM score, and deterioration-with-time rates for each RPM score for victims awaiting transport and treatment and the availability and timing of transport and treatment services.

42 Claims, 2 Drawing Sheets

U.S. PATENT DOCUMENTS

| | | | |
|---|---|---|---|
| 6,499,658 B2 * | 12/2002 | Goetz et al. | 235/385 |
| 6,804,656 B1 * | 10/2004 | Rosenfeld et al. | 705/3 |
| 2002/0011518 A1 | 1/2002 | Goetz et al. | 235/385 |
| 2002/0153413 A1 | 10/2002 | Piatek et al. | 235/375 |
| 2005/0177393 A1 | 8/2005 | Sacco et al. | |

FOREIGN PATENT DOCUMENTS

| | | |
|---|---|---|
| JP | 11-95648 | 9/1999 |

OTHER PUBLICATIONS

Strosberg, Martin A. "Intensive Care Units in the Triage Mode: An Organizational Perspective." Hospital and Health Services Administration; Spring 1991; p. 95.*

Howard R. Champion, F.R.C.S., F.A.C.S., A Revision of the Trauma Score, The Journal Of Trauma, 1989, vol. 29, No. 5, pp. 623-629.

CERT-LA S.T.A.R.T., "Simple triage and rapid treatment," *CERT-Los Angeles*, Nov. 27, 2002, http://www.cert-lacom, 8 pages.

EMMCO West, "START's the choice in the EMMCO West Region," Nov. 27, 2002, http://www.emmco,org, 2 pages.

Disaster Medical System, "Triage System, Function 7: Coordination of pre-hospital emergency services," Nov. 27, 2002, http://www.mvemsa.com, 4 pages.

Disaster Response: principles of preparation and coordination, "Triage," Apr. 3, 2003, *Chapter 8*, http://216.202.128.19/dr/disaster-Response.nsf, 23 pages.

MS, "Mass casualty incidents and start triage," Nov. 27, 2002, Nov. 27, 2002, http://www.co.broward.fl.us, Nov. 27, 2002, 14 pages.

Mass Casualty Incident Program, "Initial triage training," sponsored by A.E.M.S., Nov. 27, 2002, http://www.gc.maricopa,edu, 30 pages.

START, "Simple triage and rapid treatment," *Student Manual*, 23 pages.

Steger, M.R., "Emergency medical services, prehospital triage," *J. Emergency Care*, Apr. 3, 2003, http://www.emsmagazine.com, 8 pages.

* cited by examiner

METHOD AND SYSTEM OF MASS AND MULTIPLE CASUALTY TRIAGE

RELATED APPLICATIONS

This application claims benefit of U.S. Provisional Application Ser. Nos. 60/367,527 and 60/406,225, filed Mar. 22, 2002 and Aug. 25, 2002, respectively, each entitled, "A METHOD AND SYSTEM OF MASS CASUALTY TRIAGE PRIORITIZATION."

FIELD OF THE INVENTION

The present invention relates generally to multiple and mass casualty triage, and more particularly to a method and system that determines, for multiple casualty incidents, an efficient triage and transport plan that optimizes survivability.

BACKGROUND OF THE INVENTION

A multiple or mass casualty incident can generally be defined as an emergency or disaster where the number of patients or victims exceeds or taxes available resources, or where resource access is restricted or limited or where resources have to be staged. In contrast to routine emergencies, efficiently responding to a mass casualty incident requires triage protocol and procedures for effectively allocating the limited resources.

Triage, from the French verb trier, means to sort, and is the foundation of mass or multiple casualty management. Traditionally, medical attention and transportation to a next level of care is given first to those with the most urgent conditions. While this is appropriate in circumstances when resources are available for the immediate care of all victims, this does not necessary utilize resources most effectively when resources are limited.

The goal in the most widely used methods of mass casualty triage is typically to "do the greatest good for the greatest number". This goal is not very explicit. A more tangible and measurable goal is to maximize the saving of lives. Achieving this explicit goal requires the maximum utilization of transport and treatment resources in consideration of the timing and availability of those resources, the severity of the injuries of the victims, and their deterioration should care and transport to the next level of care be delayed as a result of resource limitations.

Accordingly, triage shall be referred to herein as an organized evaluation of all casualties to prioritize treatment and/or transport of the casualties. Further, triage includes the consideration for the availability and timing of treatment and transport resources.

When casualties are generated in large numbers, as in a mass casualty incident, local medical resources can easily be overwhelmed. The scene is often in chaos, and the response can be disorganized. As such, the efficient use of resources is compromised, with emergency response personnel left to do the best they can. There is no single, standard, or universal method of triage to support these efforts.

The triage method most widely recognized and used is known as "START," which stands for "Simple Triage and Rapid Transport." START, and its many close variations, categorizes patients into four groups: Immediates, Delayed, Ambulatory or Walking, and Expectant, which are differentiated at the scene through color coded tags. Red (Immediate) patients are those categorized as critically injured, those having problems requiring immediate intervention. These victims are given the highest priority for transport and treatment. Yellow (Delayed) patients are injured, requiring some degree of medical attention, but are not expected to die within the first hour if care is delayed. These victims would be transported once all the Reds have been moved from the scene. Delayed patients are not ambulatory, usually requiring a stretcher for transportation. Green (Ambulatory) patients are not critically injured, and can walk and care for themselves. Black (Expectant) patients are deceased, or have such catastrophic injuries that survival is not expected.

START, and its many variations, provides direction for emergency responders at the scene of an incident. START directs that anyone who can walk be tagged Green and collectively moved to a safe place. Next, remaining casualties are moved to a casualty collection area and rapidly assessed. If a casualty is not breathing, an airway is opened manually. If the patient remains apneic, they are tagged Black; if they begin breathing, they are tagged Red. Patients who are breathing and have a respiratory rate above 30 are tagged Red. If respiration is below 30, circulatory status is assessed. If capillary refill takes more than 2 seconds, the patient is tagged Red. If capillary refill takes less than 2 seconds, mental status is assessed. Patients who can follow simple commands, such as handgrips, are tagged Yellow. Patients who cannot follow simple commands are tagged Red. From the casualty collection area, patients are often then moved to a dispatch area, and later transported as resources provide.

Although START is a widely recognized triage system, it has several limitations. First, START does not consider resource availability in its process. Red tagged victims are transported first, for higher level treatment, regardless of the number of victims or the availability of transport and treatment.

Second, START does not differentiate the severity of victim injuries within its categories, and there can be a wide disparity of severity within a START category. Some casualties are categorized Immediate because of a single measure, and some due to multiple measures, yet all are grouped together, even if actual criticality substantially differs. For example, an unconscious victim is immediately classified as a Red. This patient might have only a mild concussion and might regain consciousness without intervention. Another patient might be unconscious, but also has severe respiratory problems and an accelerated heart rate. START makes no differentiation between these two even though the severity is strikingly different.

Third, START does not consider a patient's survival probability in making triage decisions. This leads to less than accurate prioritization, and a less than optimal resulting percent of survivability. For example, a Red tag victim with very little hope of surviving the trip to the hospital might be the first assigned for transport from the scene, possibly wasting valuable resources. Likewise, a Red tagged victim with very high survival probability might be sent first, even though another victim might benefit more from immediate transport.

Fourth, START does not consider the likely deterioration of victims remaining at the scene while other victims receive transport priority. A victim's survival probability is likely to decline if that victim has to wait at the scene, and this deterioration is victim and injury dependant. A serious limitation of START is that "saveable" Red and Yellow tagged victims might be left at the scene deteriorating while higher priority, but more critically injured victims, receive the limited transport and treatment resources.

Finally, START's goal is not measurable, and therefore not attainable. START's goal is to "do the greatest good for the greatest number." This is well intentioned, but is not precise or explicit. An explicit, measurable goal, such as maximizing the saving of lives, lends itself to review and accountability. With the overlay of constraints of transport and treatment resources, achieving this goal becomes a more rigorous process.

SUMMARY OF THE INVENTION

The present invention is a method and system of triage that determines a severity score for each patient quickly and accurately, and provides a treatment prioritization plan that considers and includes all casualties and all available resources to maximize total survivability, in some cases resulting in as many as seven times the survivability of current triage methods. The present invention includes a score-based mathematical algorithm for resource-constrained triage that explicitly maximizes the saving of lives in consideration of victim injury severity, victim survival probabilities, victim deterioration rates, and resource availability.

The present invention provides a prioritization plan that identifies a specific number of casualties, and the severity score of each casualty, for treatment and/or transport in any given period of resource availability. The computer model of the present invention solves instantaneously, even for large-scale casualty incidents, and is dynamic, as the model can be solved and resolved in real time as victims, resources, and conditions change.

In one aspect of the present invention, a method of mass casualty triage establishes a casualty severity score for each of a plurality of victims, then determines an order of treatment for each of the plurality of victims through consideration of the casualty severity score and resource availability. Any of a number of casualty scoring techniques, either known or to be developed, could be employed. For instance, the casualty severity score could include a sum of coded values assigned for each of a victim's respiratory rate, pulse rate, and best motor response. Or, the casualty severity score could include a refinement of categorical scoring method employed in a triage method known as START. Or, the categorical scoring method could be the Revised Trauma Score, Revised Trauma Score II, or variations thereof. Next, determining an order of treatment for each of the plurality of victims could involve mathematical or analytical programming techniques, such as but not limited to dynamic or linear programming formulations. The method could further calculate a number of expected survivors of a respective casualty incident.

In another aspect of the present invention, a triage method establishes a casualty severity score for each of a plurality of casualties, and then determines an order of treatment for each of the plurality of casualties through consideration of resource availability, the casualty severity scores, and casualty severity score deterioration rates resulting from time periods of transport and/or treatment delay. The casualty severity score deterioration rates, or victim deterioration-with-time rates, could be assumed, could be data-based, or could be determined through consideration of factors selected from one or more of an availability of state-of-the-art, or lesser levels of treatment; a cause of a casualty incident; a type of anatomic injury incurred by the victim; an age of the victim; treatment available at the incident scene; treatment available at other facilities; distances to the other facilities; and, facilities or equipment available for performance of casualty management.

In another aspect of the present invention, a triage method first assesses a respiratory rate, pulse rate, and best motor response for each of a plurality of casualties and assigns a coded value for each based on the assessment. A severity score is then established for each of the plurality of casualties by summing the coded values. Based on the total score, a survival probability is assigned to each severity score. Then, mathematical or analytical programming techniques are used to determine an order of treatment for each of the plurality of casualties. A number of expected survivors of a casualty incident can also be determined by the mathematical or analytical programming techniques.

In another aspect of the present invention, when determining the order of treatment and/or calculating the number of expected survivors, the mathematical or analytical programming techniques can consider one or more of the severity scores, the time periods of treatment delay resulting from constrained resources, the survival probabilities, and the deterioration rates applied to the severity scores due to the time periods of treatment delay. Further, the survival probability can be assumed, can be data-based, can be based upon at least one characteristic of a respective casualty or of an incident responsible for the casualty, or can be determined through consideration of one or more of an availability of state-of-the-art, or lesser levels of treatment, a type of anatomic injury incurred by the victim; an age of the victim, treatment available at the incident scene, treatment available at other facilities, distances to the other facilities, and/or facilities or equipment available for performance of casualty management.

In another aspect of the present invention, computer software is provided to perform any of the triage methods of the present invention. In still another aspect, reference and training materials are provided, as well as a training and instructional program, the reference materials and training program directed to teaching first responders the triage methods of the present invention. The instructional program can include case studies that present trauma scenarios and injury data, the case studies challenging trainees to determine an order of treatment, and providing a likely survivability result based upon the determined order of treatment. Further, the instructional methods of the programs can include hints, leading questions, other "best learning practices" pedagogy, or additional information in response to a determined order of treatment, to improve the resulting survivability result, and to hone the skills of the trainees.

BRIEF DESCRIPTION OF THE DRAWINGS

For the purpose of illustrating the invention, there is shown in the drawing one embodiment of the present invention; it being understood, however, that this invention is not limited to the precise arrangements and instrumentalities shown.

DETAILED DESCRIPTION OF THE INVENTION

The present invention provides a method of managing triage for multiple and mass casualty incidents. Generally, the method of the present invention includes the following procedures:

1. Determining a casualty severity score for each victim; and
2. Determining a priority order of treatment for the victims.

The goal of the present invention is to maximize the expected number of survivors in any multiple or mass casualty or resource constrained triage incident. Achieving this goal requires, as resources become available, determining an order upon which victims will be treated, or upon which victims will be transported for treatment, or some combination thereof.

Accordingly, determining a priority order of treatment could occur at the incident scene, and be directed to an order of victim transport to a medical facility. Or, the priority order could be directed to an order of initial treatment at the incident scene, with or without further transport to a medical facility. Or, determining a casualty severity score for each victim, and determining an order of treatment, could occur at an emergency room, or other medical facility intake area, to facilitate optimal triage management at a more specific and localized area remote from an casualty incident scene.

In a catastrophic event, a multiple or mass casualty incident, or any casualty incident where transport and treatment resources are limited, a major issue confronted by triage personnel is that not all of the injured can receive state-of-art treatment instantaneously due to limited resources, either at the incident scene or at further echelons of care, such as holding areas, emergency departments, and resuscitation bays. For the foregoing reasons, the present invention contemplates use in any location, and for any incident, where optimal triage management procedures would result in maximizing victim survival.

For purposes of resolving a triage problem, the present invention recognizes time periods, each time period represented by an amount of resources available for treatment and/or transport of casualties. Due to the likely limitation on resources, certain casualties may wait one or more time periods before receiving treatment by or transport to upper echelons of care. Time periods may be of variable length, and the resources available during any one time period may or may not be equal to the resources available during other time periods. The present invention recognizes the importance of full and efficient utilization of resources across all time periods, and contemplates employment of certain problem solving methods to ensure full and efficient utilization of resources across all time periods. For instance, if time period length is essentially defined by emergency transport time in route to a certain upper echelon care facility, the present invention could employ problem solving techniques such as Dijkstra's method to minimize time in route.

In one aspect of the present invention, the casualty severity scoring method used is "RPM," a method using coded values of a casualty's Respiratory rate, Pulse rate, and best Motor response (a measure of neurological status). It is envisioned that the present invention could employ other methods of casualty scoring, or variations of the RPM model detailed herein, as various scoring applications, either known or to be developed, could easily be adapted to the broad concepts of the present invention. By way of example, the present invention could alternatively incorporate Revised Trauma Score (RTS), the recognized triage standard of the American College of Surgeons. Further, several other abbreviated physiologic severity scores exist and could be incorporated into the present invention, including RPV (based on respiratory rate, pulse rate, and best verbal response), body-region-injury dependent RPV, body-region-injury dependent scores (based on respiratory rate and pulse rate), the Glasgow Coma Scale and best motor response. Also, a scoring methodology could be developed and used based upon the assessment methods currently employed in START.

In another aspect of the present invention, the treatment and triage priorities are then determined from analytical, mathematical, and/or optimization techniques, such as dynamic programming or linear programming, and can incorporate, for greater precision, one or more of data-based estimates of casualty survival probabilities and victim deterioration-with-time rates. The data could be accumulated from previous injury scene data for trauma patients, such as trauma registries, or other mass casualty incidents, or could be estimated based on experts' subjective opinions, with survival probabilities and deterioration rates determined using standard statistical methods.

If incorporating casualty survival probabilities and/or deterioration-with-time rates into the model, a probability or rate could be determined for and used with each of the RPM values. If desired, for greater precision, the survival probability or deterioration rate could be determined using data that considers any one or more of a variety of factors, such as but not limited to an availability of state-of-the-art, or lesser levels of treatment; a cause of or weapon used to create the mass casualty incident (such as a weapon of mass destruction, or a natural disaster); type of anatomic injury incurred by the casualty (such as blunt or penetrating injury, or trauma from blast, chemical, radiological or biological incident); age or age range of the casualty; treatment available at the incident scene, and/or at locations of higher echelons of care; distances to the higher echelons of care; and facilities or equipment available for performance of the casualty management itself. The above list of factors is exemplary, and not limiting, as the casualty survival probabilities and victim deterioration-with-time rates could be a work in progress, continually refined based upon ever-increasing data directed to the above-referenced factors, to other existing factors having available data, or to factors yet to be developed with consideration of the concepts of the present invention.

In another aspect of the present invention, either dynamic or linear programming can be used to determine a priority of treatment for the casualties, each operating irrespective of the specific factors chosen above. The dynamic and linear programming formulations are each directed to maximizing the number of victims saved across all time periods, subject to constraints on available resources in each time period and the number of victims of particular severity score available within each time period. The dynamic and linear programming approaches provide essentially the same optimal result, the difference being approach and method of solution. The present invention also envisions using other methods to determine treatment priorities, including heuristic methods, such as but not limited to search theory based solutions and greedy approaches operating to optimize the number of survivors.

For further precision, the dynamic and/or linear programming formulations could maximize the number of victims saved across all time periods by further considering a type of trauma experienced by the victim, a classification of the victim, and/or a type of care center appropriate for and available to the victim. For instance, specific embodiments could consider, in determining prioritization, that the victim has experienced blunt or penetrating trauma, or blast, chemical, radiological, or biological trauma. Considering the type of trauma experienced, in addition to and in conjunction with the consideration of severity score, could further aid the maximization of victims saved by optimizing the prioritizations determined. A class of the victim could consider age and/or previous health conditions of the victim, and incorporate same into the considerations above. For type of care center, the dynamic or linear programming could determine a priority of treatment based upon a further consideration of matching a type of injury to specific care centers and/or doctors appropriate for and available to the victim, to avoid inefficiencies possible when a victim is transported or received for treatment, but then cannot receive same because needed specialty care is not available at that time, or at that location.

In another aspect, the present invention also includes software to encapsulate the methods expressed herein, the software also providing management assistance for performance of each step of the respective method employed. The software would be compatible with standard personal and laptop computers, and compatible with mobile devices, such as PDAs (i.e. Personal Digital Assistants), presently existing or to be developed, the software providing management assistance and method capability at the incident scene, at one or more remote locations, or at any combination thereof.

In still another aspect of the present invention, triage strategy is determined by software at a central processing location, with coordinated programming by hand held devices located at the incident scene. This aspect employs fully automated dispatch, matching victims with transport and hospital resources through automated data communication. Alternatively, the methods of the present invention could be carried out using a command center approach, where two-way radios communicate necessary data to central control. Further, a simulation driven, rule based protocol could be established having control in the field. In the simulation driven approach, emergency personnel would arrive at a casualty event and quickly characterize the scene and the resources available (i.e., generally characterize a number and a severity of casualties in relation to resource availability, thereby determining a degree of resource constraint). Next, as individual victim assessment begins, the characterization of the entire event is associated with one of several (or more) protocols. The protocol provides direction regarding an order of treatment necessary to maximize total survivability for a given casualty event, and each protocol is pre-established based on simulations including certain assumptions, or facts, about the given casualty event. The quick characterization of the entire event guides the emergency personnel in a selection of a pre-established protocol most closely resembling the casualty incident at issue.

By way of example, the following describes certain aspects of the present invention:

RPM Scoring

RPM is the sum of coded values of respiratory rate (RR), pulse rate (PR), and best motor response (BMR). In one embodiment, the coded values are:

| RR: | 0, | 1-9, | 10-24, | 25-35, | 35+ |
|---|---|---|---|---|---|
| Coded Values | 0 | 1 | 4 | 3 | 2 |
| PR: | 0, | 1-40, | 41-60, | 61-120, | 120+ |
| Coded Values | 0 | 1 | 2 | 4 | 3 |
| BMR: | None, | Ext/Flex, | Withdraws, | Localizes, | Obeys Commands |
| Coded Values | 0 | 1 | 2 | 3 | 4 |

In this embodiment, RPM takes on integer values from zero (0) to twelve (12). RR is measured in breaths/minute, and is implemented by measuring breaths for fifteen (15) seconds and multiplying by four (4). PR is measured in beats/minute, and is implemented by measuring beats for fifteen (15) seconds and multiplying by four (4). BMR assesses the ability of the casualty to respond with movement to stimuli as follows:

Obeys Commands: This requires an ability to comprehend instructions given by verbal command. The casualty must perform the specific movement requested. The following could be a typical routine: the first verbal command is "raise your hand"; if the casualty does so, the assessment is Obeys Commands; if not, the second command is "squeeze my hand"; if the casualty does so, the assessment is Obeys Commands; if not, a painful stimulus, preferably a "nail bed" stimulus, is applied to try to produce a response.

Localizes pain: After painful stimulation, the casualty reaches and/or tries to remove the source of pain.

Withdraws: After painful stimulation, there is flexion of elbow, with rapid movement and no muscle stiffiess, and the arm is drawn away from the trunk.

Flexion: After painful stimulation, the elbow flexes slowly accompanied by stiffness, and the forearm and hand remain held against the body.

Extension: After painful stimulation, the legs and arms extend. This movement is accompanied by stiffness and there is internal rotation of the shoulder and forearm.

None: No response to pain.

In one embodiment of the invention, the following is a sample calculation of RPM: If RR=16, PR=50, and BMR is "Obeys Commands", then the coded values are 4, 2, and 4 (from above), and the sum of the coded values (the RPM) equals ten (10).

Casualty Survival Probabilities

By way of example, in one embodiment of the present invention the following are the survival probabilities associated with each RPM value. The survival probabilities presented below are based upon data compiled from various hospital and state-wide trauma statistics involving thousands of casualties.

| RPM Value | Survival Probability |
|---|---|
| 12 | .992 |
| 11 | .985 |
| 10 | .970 |
| 9 | .970 |
| 8 | .910 |
| 7 | .830 |
| 6 | .720 |
| 5 | .570 |
| 4 | .410 |
| 3 | .270 |
| 2 | .160 |
| 1 | .090 |
| 0 | .052 |

Victim Deterioration-with-Time Rates

By way of example, in one embodiment of the present invention the following represents victim deterioration-with-time rates for casualties who remain at the incident scene and continue to receive first respondent treatment at most. The deterioration-with-time rates presented below are based upon interviews with trauma center personnel directed to experiences and statistics of trauma victims and their respective treatment.

| RPM values | Score Point Decrease/30 minutes |
|---|---|
| 11-12 | 1** |
| 8-10 | 1 |
| 5-7 | 2 |
| 3, 4 | 3 |
| 2 | 2 |

| RPM values | Score Point Decrease/30 minutes |
|---|---|
| 1 | 1 |
| 0 | 0 |

**For RPM values of 11-12, the score point decrease of one (1) occurs over two (2) thirty (30) minute time periods.

Note:
an example helps to interpret the table. A victim with a first assessment RPM value of eight (8) would have a value of seven (7) thirty (30) minutes after the first assessment, and a value of five (5) one (1) hour after the first assessment with an associated decrease in survival probability from .91 to .57.

Figure 1:
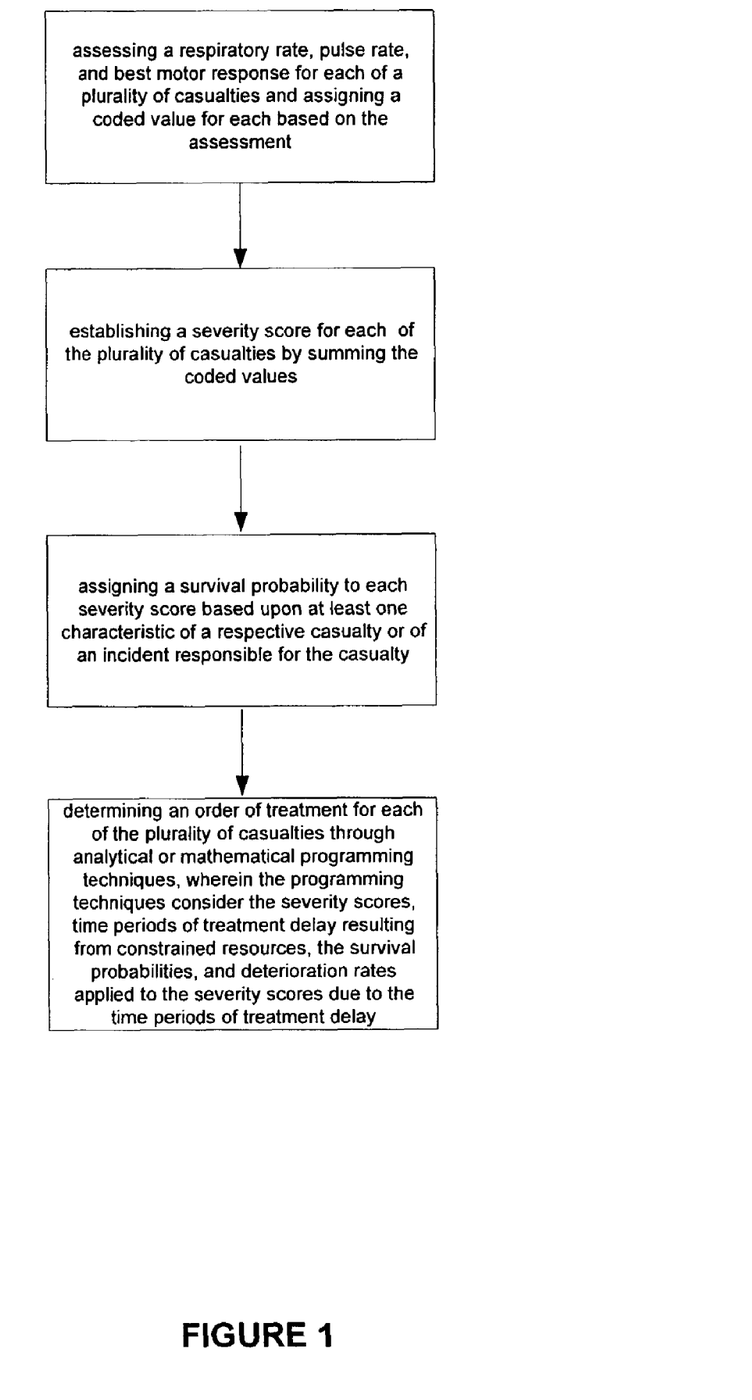
FIG. 1 is a flow diagram illustrating a method of triage in accordance with one embodiment of the present invention.
Figure 2:
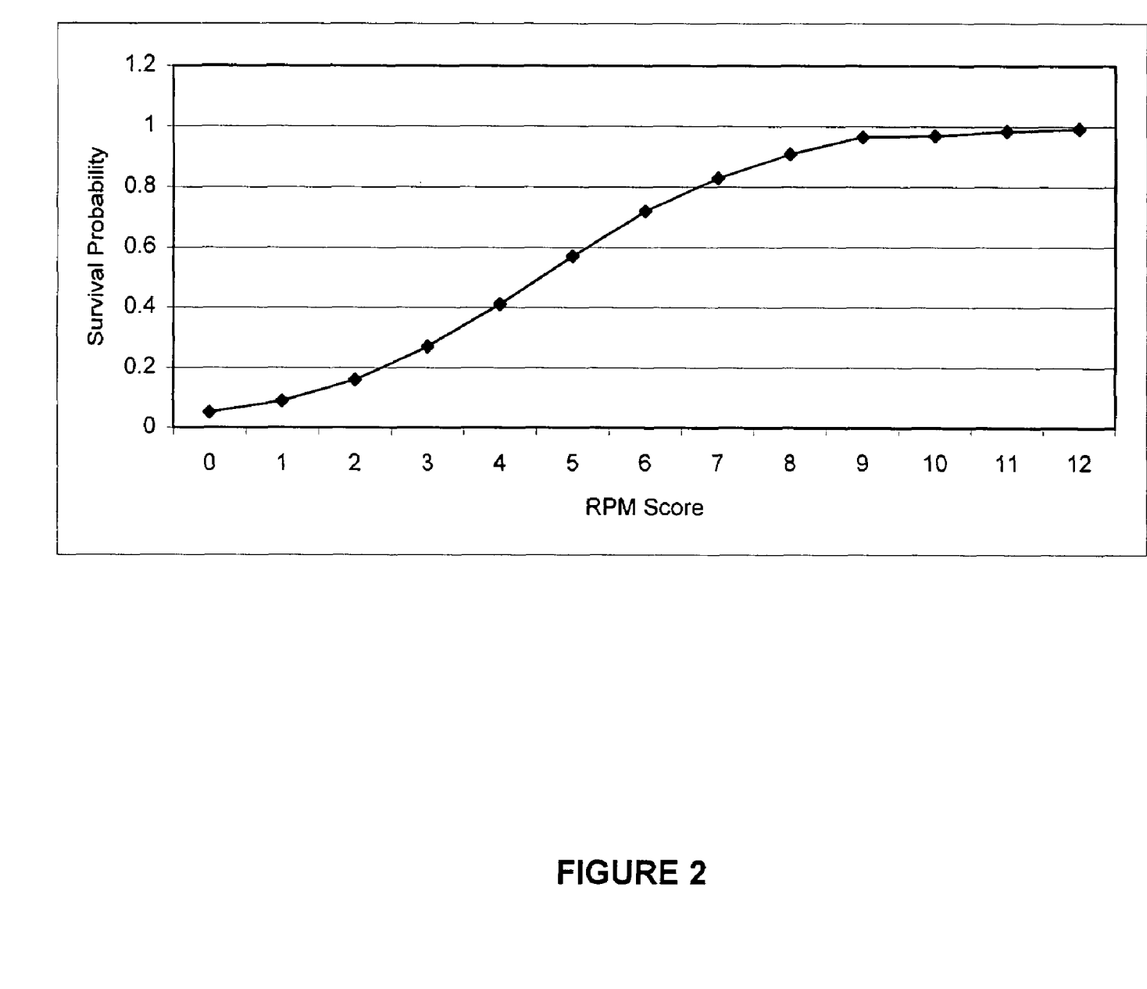
FIG. 2 is a graph illustrating a relationship between survival probability and casualty severity score in accordance with an embodiment of the present invention.

Casualty Survival Probability in Relation to Victim Deterioration-With-Time Rates FIG. 2 illustrates graphically the specific survival probabilities presented above in relation to respective RPM score. The plotted points of FIG. 2 create an "S"-shaped curve, the "S"-shaped curve including somewhat leveled-off survival probabilities at the high and at the low end of the RPM values, but demonstrating a substantial decrease in, or declining, survival probability between the RPM scores of approximately seven (7) and four (4). Combining this finding with the specific deterioration-with-time rates presented above, it can be seen that, over the entire range of RPM scores, there is a crucial and central range of rapid deterioration in survival probability for RPM scores between 7 and 4).

Determining Treatment and/or Transportation Prioritization

By way of continued example, in one embodiment of the present invention casualty prioritization for treatment and/or transportation is determined by combining: 1) RPM severity scoring and associated survival probability estimates; 2) victim deterioration-with-time rates for those casualties remaining at the incident scene and receiving only first-respondent treatment; and 3) dynamic programming and linear programming.

The RPM value is assessed for each casualty by first responders. The underlying assumption is that the human body responds in specific ways to trauma, depending on the severity of the trauma. More severe trauma results in physiological changes from normal which are greater than those associated with less serious trauma. As with all physiologically based severity scoring, the time interval between the trauma and the assessment can affect the severity score, since the response of body systems to trauma is not instantaneous, but graded over time. There is great value in serial assessments and the charting of changes in the value of assessments over time.

To complete the prioritization process, the dynamic or linear programming problem is solved, the formulation of the problem appearing below:

Stochastic Dynamic Programming Formulation

Let O(N)=Maximum Expected number of Survivors for N casualties in the event where $N=(n_0, n_1, \ldots, n_k)$; $n_i$=the number of victims with a severity score equal to i, where i=0 ... k. The problem can then be formulated as a multi-dimensional, stochastic dynamic programming problem as follows:

$$O(N)=\text{maximum[expected survivors (subset triaged first)}+O(N')](STF)$$

where, STF=subset of patients selected for first transport and/or first treatment, and $N=(n_0, n_1, \ldots, n_k)$ Notes on the formulation of this embodiment of the present invention:

1. The number of patients in the subset STF will correspond to the number of patients that can be treated by the resources in the next echelon of treatment available.

2. N is a state vector which reflects the numbers of patients not included in the first group triaged and their predicted RPM values at the time of triage for the next group.

3. The mass casualty triage problem is a multistage problem with successive stages being a selection of a subset of patients for triage to the next echelon of care. The quantity inside the brackets [ ] gives the expected number of survivors for an arbitrary selection of the first patient set to be triaged (first term inside the brackets) plus the second term inside the brackets, which is the maximum expected number of survivors "for the remaining stages" given the casualty state (status) of the remaining (nontriaged) casualties at the time of next opportunity to triage. Accordingly, the quantity inside the brackets represents one arbitrarily triaged subset (the first subset triaged) and "optimal" triaging thereafter.

The symbol $$---\underset{STF}{\text{maximum}}---$$

in front of the brackets reflects that the first subset of casualties to be treated or transported will also be optimized, thus making the entire ordering process optimal.

Linear Programming Formulation

The linear programming formulation maximizes the number of victims saved across all time periods, subject to constraints on the amount of medical resources available in each time period, and the number of victims with each severity score. Mathematically, if we let $V_{st}$=victims treated in time period t with severity score s, and $P_s$=the survival probability of treated victims with severity scores s, then the Linear Programming formulation is as follows:

$$\text{MAX} \sum_{st} P_s V_{st}$$

subject to $$\sum_t V_{st} = \text{number of victims of score } s, \text{ for all values of } s$$

$$\sum_s V_{st} <= \begin{array}{c}\text{maximum number of victims that can be treated in}\\ \text{time period } t, \text{ for all values of } s \text{ (this limits the}\\ \text{resouces).}\end{array}$$

The linear programming formulation identifies the number of victims with each score and in each time period to be treated such that the overall number of survivors is the maximum possible, given the limitation on available resources. The model of the present invention yields a completely feasible solution, solves very quickly using commercially available linear programming software, and does so even when operating under a large-scale mass casualty situation. The model of the present invention predicts survivability based on the survival probabilities used for each severity score, and is influenced by deteriorations-with-time rates as considered for the waiting victims. This formulation is easily expanded to directly include one or more of a variety of considerations, and/or to indirectly include the one or more variety of considerations through differentiated survival probabilities and/or differentiated deterioration-with-time rates. The variety of considerations could include, but would not be limited to, an availability of state-of-the-art, or lesser levels of treatment; a cause of or weapon used to create the casualty incident; type of trauma incurred by the casualty; a classification of the casualty, such as age or previous health condition; a type of care center appropriate for and available to the casualty, and/or treatment available at the incident scene; distances to the higher echelons of care; and facilities or equipment available for performance of the casualty management itself.

An Exemplary Embodiment of the present invention

By way of example, the following illustrates a possible casualty incident, and illustrates how the present invention would prioritize respective casualties for treatment in each time period to optimize total survivors over the entire event. The following embodiment has essentially equal results whether using dynamic or linear programming.

Assumptions:
a) 2600 victims
b) Of the 2600 victims, there are 200 victims in each RPM severity score category (RPM=0 through 12) (13 scores×200=2600)
c) 500 victims can be treated in each period
d) Victims will experience the following severity score deterioration-with-time for each time period:

| RPM value at beginning of time period | Score Point Decrease per time period |
|---|---|
| 8-12 | 1 |
| 5-7 | 2 |
| 3-4 | 3 |
| 2 | 2 |
| 1 | 1 |
| 0 | 0 |

Optimal Triage Protocol in accordance with dynamic or linear programming:
Time period 1
  Treat 200 with score of 5
  Treat 200 with score of 6
  Treat 100 with score of 7
Time period 2
  Treat 100 with original score of 7 (now score of 5)
  Treat 200 with original score of 8 (now score of 7)
  Treat 200 with original score of 9 (now score of 8)
Time Period 3
  Treat 200 with original score of 10 (now score of 8)
  Treat 200 with original score of 11 (now score of 9)
  Treat 100 with original score of 12 (now score of 10)
Time period 4
  Treat 100 with original score of 12 (now score of 9)
  Treat any victims still surviving (now score of 0)

Treatment or transportation continues through added time periods until all victims are triaged. The present invention is expected to save 1362 of the 2600 casualties when operating within, the assumptions presented above.

Presented below is a continuation of the exemplary embodiment (i.e., 2600 victims, including 200 in each RPM category), illustrating how resource constraints impact survivor results and impact an order of treatment that maximizes survivor results. A comparison of survivor results is also presented between the methodology of the present invention and the worst-first sorting philosophy of START. For instance, in column 2, where 50 victims can be treated in each time period, the methodology of the present invention directs that casualties with an RPM score of 11 are treated in each of the first 4 time periods (50 per period), thereby first accounting for all casualties with an RPM score of 11; then casualties with an RPM score of 12 are treated in each of the next 4 time periods (50 per period), with continued treatment through added time periods as survivors permit. The scenario detailed above, where 500 victims can be treated in each time period, is also shown in table form, below, in column 5.

| Victims in Each RPM Category | 200 | 200 | 200 | 200 | 200 |
|---|---|---|---|---|---|
| Resources in Each Time Period | 50 | 100 | 200 | 500 | 800 |
| Treatment Order (by RPM score per time period) | | | | | |
| $1^{st}$ | 11 | 9 | 7 | 5, 6, 7 | 4, 5, 6, 7 |
| $2^{nd}$ | 11 | 10 | 8 | 7, 8, 9 | 8, 9, 10, 11 |
| $3^{rd}$ | 11 | 10 | 9 | 10, 11, 12 | 12 |
| $4^{th}$ | 11 | 11 | 10 | 12, 4, 3 | — |
| $5^{th}$ | 12 | 11 | 11 | 2, 1, 0 | — |
| $6^{th}$ | 12 | 12 | 12 | — | — |
| $7^{th}$ | 12 | 12 | — | — | — |
| $8^{th}$ | 12 | — | — | — | — |
| Max Saves | 1582 | 1582 | 1582 | 1582 | 1582 |
| Present Invention Saves | 434 | 693 | 1068 | 1362 | 1474 |
| Worst First | 135 | 135 | 135 | 720 | 1224 |

Comparison of START and the Present Invention

Recall that START employs severity categorizing based on three observations: respiration, perfusion, and mental status. In START, severity categorization is not specifically delineated, nor is it a computed score. Rather, START provides a method for quickly classifying a victim into one of four categories. Again, the categories are Ambulatory (or Minor), Immediate, Expectant (or Dead), and Delayed.

Ambulatory: All casualties are asked to stand up and walk to a specific area. All that can are designated as ambulatory or minor.

Immediate: A casualty is designated Immediate if breathing with a respiratory rate greater than 30 breaths/minute; OR, pulse is absent for 5 to 10 seconds or is "irregular"; OR, the victim cannot follow the commands "open your eyes", "close your eyes", or "squeeze my hand".

Expectant: A casualty is not breathing and does not start to breath with simple airway maneuvers.

Delayed: Any victim who does not fit into any of the three other categories

START employs the following treatment and/or transportation prioritization strategy: treat all immediates first, then delayeds, then others as opportunity provides. START does not distinguish among the Immediates, or among the Delayeds, with respect to prioritization for transport and upper echelon treatment. Prioritization for treatment and/or transportation is arbitrary among the Immediates, and then among the Delayeds. This can and does result in substantially more deaths than necessary, as demonstrated herein by example:

Immediates, in accordance with START doctrine, can take on the following present invention RPM component values: coded RR values of 2, 3, and 0; PR coded values of 1, 2, 3, and 4; and BMR values of 0, 1, 2, and 3. Accordingly, START Immediates can take on present invention RPM values between 1 through 10.

Delayeds, in accordance with START doctrine, can take on the following present invention RPM component values; coded RR values of 1, 3, and 4; coded PR values of 1, 2, 3, and 4; and a coded BMR value of 4. Accordingly, START Delayeds can take on present invention RPM values between 6 and 12.

As mentioned, START then makes no further effort to prioritize casualties categorized as Delayeds (other than the general categorization of being a Delayed) for treatment and/or transport, except to categorize them as an Immediate upon a qualifying reassessment.

The method of the present invention, however, distinguishes every casualty by specific severity score, and then rationally prioritizes each, based upon specific score, for treatment and/or transport. The method of the present invention can result in substantially more survivors than START, perhaps as many as seven times the number of survivors.

By way of example (this example is suggestive and not a typical): suppose there are 500 Immediates with present invention RPMs of 1 (survival probability=0.09 with state-of-art treatment); 500 Delayeds with present invention RPMs of 6 (survival probability=0.72 with state-of-art treatment); and 500 casualties can be treated at a time. As prescribed by doctrine, START triages the Immediates first (without taking into account survival probabilities or deterioration-with-time rates to determine priority), and experiences 45 survivors (0.090×500) among the 500 Immediates. START then experiences 205 survivors (0.410×500) one-half hour later upon triaging the 500 Delayeds (a survival probability of 0.410 is used because the 500 Delayeds have deteriorated to a present invention RPM of 4 in the one-half hour). Therefore, START saves 250 casualties.

The doctrine of the present invention directs the sending of the Delayeds first, experiencing 360 survivors (0.720×500), and experiencing (one-half hour later) an additional 26 survivors (0.052×500) from the Immediates, who began with RPM values of 1 and have deteriorated to a present invention RPM of 0. Therefore, the present invention saves 386 casualties.

A Variation of START as an Embodiment of the Present Invention

Based upon the less than optimal severity categorization of casualties in START, and the lack of ordering of treatment to maximize total survivors, the present invention also includes, in one aspect, a refinement of the START methodology to optimize total survivability. In this embodiment, incident victims are first categorized into one of the four START categories (Ambulatory, Immediate, Expectant, and Delayed) as described above, and by the START methodology described above.

Next, for those in the Immediate and Delayed categories, the respiratory, perfusion, and mental status observations are assessed for each victim in relation to an anatomic region of the body incurring injury, and survival probability rates are determined and assigned to each Immediate and Delayed casualty based upon the respiratory, perfusion, and mental status observations in relation to the anatomic region of the body incurring injury. The survival probability rates used can be assumed, can be data-based, or can be specifically compiled from existing trauma data-bases.

Then, each Immediate and Delayed casualty is further partitioned into one or more subcategories based upon the survival probability rate determined and assigned, so that victims grouped together (in the subcategories) have a lesser variation in likelihood of survival. The refinement of the Immediate and Delayed START categories, into subcategories, provides a more precise indicator of casualty severity for each Immediate and Delayed casualty, leading to a determination of an order of treatment providing maximum survivability. From this point, any of the methods of the present invention described above to determine an order of treatment can be employed to prioritize each of the subcategories of Immediate and Delayed casualties. The result is a more effective START triage method, employing several aspects of the present invention, directed to maximizing the number of survivors of a casualty incident.

An Instructional Program Directed to the Present Invention

In another aspect of the present invention, a training method and program is directed to training first responders in the triage methods of the present invention. First responders are defined generally as any participant in a triage operation, or any emergency care personnel involved in a casualty incident. The training methods and program could include case studies providing trainees with a variety of simulated triage experiences, each providing pre-determined trauma scenarios and injury data, such as casualty severity scores and resource availability, to challenge trainees to make triage decisions at the "incident scene", including determinations directed to an order of treatment and/or transportation for each of the incident casualties. For each triage decision made, the trainees could receive scored results based upon their decisions. The results could be in the form of a likely number of survivors resulting from the respective triage decisions.

Trainees (first responders) can initially use their past training and best judgment to direct their decision-making, then the training program could provide hints, leading questions, and/or additional information (i.e., general assistance) to guide and accelerate the learning process. The general assistance efficiently focuses the trainees on important features and method steps of the present invention, by helping the trainees discover flaws in their pre-training approach. The training process of the present invention can provide a dramatic learning experience, as trainees will experience an outcome based on their simulated triage decisions in terms of a number of survivors. Not only will the trainees learn the triage methods of the present invention, but they will fully understand and appreciate its benefits. Repetitive simulated training employing various case studies will hone skills, resulting in trainees experienced in the mechanics of the triage protocols of the present invention, confident in the outcome of the protocols, and prepared to use them correctly in a crisis. Reference materials could be provided, and case studies could be presented through video and animation, and offered, if desired, online.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. A method of triage for determining an order of transport from a mass casualty incident that maximizes the number of survivors of the mass casualty incident, the method comprising the steps of:

receiving, from incident personnel at a mass casualty scene, a casualty severity score for each of a plurality of victims at the mass casualty scene;

inputting each casualty severity score into a computer;

receiving information indicative of medical transport resources available for the plurality of victims;

inputting the information indicative of medical transport resources available into a computer; and determining by a computer implemented decision logic an order of transport for treatment for each of the plurality of victims, wherein the decision logic mathematically factors the casualty severity scores and the resources available for the plurality of victims.

2. The method of claim 1, wherein the casualty severity score includes a sum of coded values, where a coded value is assigned for each of a victim's respiratory rate, pulse rate, and best motor response.

3. The method of claim 2, wherein best motor response is a measure of neurological status.

4. The method of claim 1, wherein establishing the casualty severity score includes:

categorizing each of the plurality of victims into one of four categories, wherein the four categories are Ambulatory, Immediate, Expectant, and Delayed, as employed in a triage method known as START;

assessing, for each of the plurality of victims categorized in the Immediate and Delayed categories of START, respiratory, perfusion, and mental status in relation to a physiologic or anatomic region of the body incurring injury;

determining and assigning a survival probability rate for each of the plurality of victims categorized in the Immediate and Delayed categories, wherein the survival probability rate represents the casualty severity score.

5. The method of claim 4, wherein determining the survival probability rate considers the respiratory, perfusion, and mental status assessments in relation to the physiologic or anatomic region of the body incurring injury.

6. The method of claim 1, wherein determining an order of transport for treatment employs a score-based mathematical algorithm for resource-constrained triage.

7. The method of claim 1, wherein determining an order of transport for treatment for each of the plurality of victims involves analytical or mathematical programming techniques.

8. The method of claim 7, wherein the analytical or mathematical programming techniques consider a type of trauma experienced by each victim, a classification of each victim, and/or a type of care center appropriate for and available to each victim, to optimize the order of treatment determined.

9. The method of claim 7, wherein the analytical or mathematical programming techniques use a data-based estimate of casualty survival probability with each casualty severity score.

10. The method of claim 9, wherein the casualty survival probability is determined through consideration of factors selected from the group consisting of an availability of state-of-the-art, or lesser levels of, treatment; a cause of a casualty incident; a type of anatomic injury incurred by the victim; an age of the victim; treatment available at the incident scene; treatment available at other facilities; distances to the other facilities; and, facilities or equipment available for performance of casualty management.

11. The method of claim 7, wherein the analytical or mathematical programming techniques include victim deterioration-with-time rates for each casualty severity score based upon an amount of time a victim awaits treatment.

12. The method of claim 11, wherein the victim deterioration-with-time rates are determined through consideration of factors selected from the group consisting of an availability of state-of-the-art, or lesser levels of, treatment; a cause of a casualty incident; a type of anatomic injury incurred by the victim; an age of the victim; treatment available at the incident scene; treatment available at other facilities; distances to the other facilities; and facilities or equipment available for performance of casualty management.

13. The method of claim 1, wherein determining an order of transport for treatment for each of the plurality of victims involves a dynamic programming formulation.

14. The method of claim 13, wherein the dynamic programming formulation determines a subset of the plurality of victims to transport for treatment during each of a plurality of time periods to maximize a total number of survivors over all time periods.

15. The method of claim 1, wherein determining an order of transport for treatment for each of the plurality of victims involves a linear programming formulation.

16. The method of claim 15, wherein the linear programming formulation determines a subset of the plurality of victims to transport for treatment during each of a plurality of time periods, and identifies a severity score to associate with each of the victims in the subset, to maximize a total number of survivors over all time periods.

17. The method of claim 1, wherein:

the casualty severity score for each victim is entered into a portable computing device and communicated to a central processing location;

the information indicative of resources available for care of the victims is received at the central processing location; and the order of transport for treatment is determined at the central processing location.

18. The method of claim 17, wherein the central processing location communicates the order of transport for treatment for each of the victims to the one or more portable computing devices for display thereon to direct an ordering of the victims at the mass casualty scene for transport for treatment.

19. The method of claim 1, wherein:

the casualty severity score for each victim and the information indicative of medical transport resources available for the victims is entered into a portable computing device; and the order of transport for treatment is determined using the portable computing device.

20. A triage method for determining an order of treatment, or transport for treatment, for casualties of a mass casualty incident, to maximize the number of survivors of the mass casualty incident, the method comprising the steps of:

receiving, from incident personnel at a mass casualty scene, a casualty severity score for each of a plurality of casualties at the mass casualty scene;

inputting each casualty severity score into a computer;

receiving information indicative of medical transport resources available for the plurality of casualties;

inputting the information indicative of medical transport resources available into a computer;

determining by a computer implemented decision logic an order of treatment, or transport for treatment, for each of the plurality of casualties, wherein the decision logic mathematically factors the resources available for the plurality of casualties, the casualty severity scores, casualty severity score deterioration rates resulting from time periods of treatment delay, and one or more of a type of trauma experienced by each casualty, a classification of each casualty, and a type of care center appropriate for and available to each casualty; and communicating the order of treatment, or transport for treatment, to incident personnel for their use in directing an ordering of the casualties.

21. The method of claim 20, wherein the casualty severity score includes a sum of coded values, where a coded value is assigned for each of a victim's respiratory rate, pulse rate, and best motor response.

22. The method of claim 20, further comprising the step of calculating a number of expected survivors of the mass casualty incident.

23. A triage method for determining an order of transport from a mass casualty incident that maximizes the number of survivors of the mass casualty incident, the method comprising the steps of:

assessing one or more physiological characteristics of each of a plurality of casualties at a mass casualty scene, by incident personnel at the mass casualty scene, and receiving from the incident personnel, or separately assigning, a coded value for each of the one or more physiological characteristics;

receiving from the incident personnel, or separately establishing, a casualty severity score for each of the plurality of casualties at the mass casualty scene using the coded value(s);

inputting each casualty severity score into a computer;

receiving from the incident personnel, or separately assigning, a survival probability to each casualty severity score based upon at least one characteristic of the respective casualty or of an incident responsible for the casualty;

inputting the survival probability for each casualty severity score into a computer;

receiving information indicative of medical transport resources available for the plurality of casualties;

inputting the information indicative of medical transport resources available into a computer;

determining by a computer implemented decision logic an order of transport for treatment for each of the plurality of casualties through analytical or mathematical programming techniques, wherein the programming techniques mathematically consider the casualty severity scores, the time periods of treatment delay resulting from constrained resources available for the plurality of casualties, the survival probabilities, and deterioration rates applied to the casualty severity scores due to the time periods of treatment delay; and communicating the order of transport for treatment to incident personnel for their use in directing an ordering of the casualties at the mass casualty scene for transport from the mass casualty scene.

24. The method of claim 23, further comprising the step of calculating a number of expected survivors of the mass casualty incident through the analytical or mathematical programming techniques.

25. The method of claim 23, wherein:

the coded value for each physiological characteristic of each casualty is entered into a portable computing device;

the casualty severity score for each of the plurality of casualties is established by the portable computing device and communicated to a central processing location, or the casualty severity score for each of the plurality of casualties is established at the central processing location after reception at the central processing location of the coded value for each physiological characteristic of each casualty;

the information indicative of medical transport resources available for the victims is received at the central processing location; and the order of transport for treatment is determined by computer implemented decision logic at the central processing location.

26. A computer readable medium that configures a computer system to perform a method of triage for determining an order of transport from a mass casualty incident that maximizes the number of survivors of the mass casualty incident, the method comprising the steps of:

receiving, from incident personnel at a mass casualty scene, a casualty severity score for each of a plurality of victims at the mass casualty scene;

inputting each casualty severity score into the computer system;

receiving information indicative of medical transport resources available for the plurality of victims;

inputting the information indicative of medical transport resources available into the computer system; and determining an order of transport for treatment for each of the plurality of victims, wherein the determination mathematically factors the casualty severity scores and the medical transport resources available.

27. A computer readable medium that configures a computer system to perform a method of triage for determining an order of treatment, or transport for treatment, for casualties of a mass casualty incident, to maximize the number of survivors of the mass casualty incident, the method comprising the steps of:

receiving, from incident personnel at a mass casualty scene, a casualty severity score for each of a plurality of casualties at the mass casualty scene;

inputting each casualty severity score into the computer system;

receiving information indicative of medical transport resources available for the plurality of casualties;

inputting the information indicative of medical transport resources available into the computer system;

determining an order of treatment, or transport for treatment, for each of the plurality of casualties, wherein the determination mathematically factors the medical resources available for the plurality of casualties, the casualty severity scores, and casualty severity score deterioration rates resulting from time periods of treatment delay.

28. A computer-readable medium that configures a computer system to perform a method of triage for determining an order of transport from a mass casualty incident that maximizes the number of survivors of the mass casualty incident, the method comprising the steps of:

receiving coded values, from incident personnel at a mass casualty scene, for one or more physiological characteristics taken for each of a plurality of victims at the mass casualty scene;

inputting the coded values into the computer system;

receiving information indicative of medical transport resources available for the plurality of victims;

inputting the information indicative of medical transport resources available into the computer system;

establishing a casualty severity score for each of the plurality of victims using the coded values; and determining an order of transport for treatment for each of the plurality of victims, wherein the determination mathematically factors the medical transport resources available for the plurality of victims and the casualty severity scores.

29. A computer readable medium that configures a computer system to perform a method of triage for determining an order of transport from a mass casualty incident that maximizes the number of survivors of the mass casualty incident, the method comprising the steps of:
 receiving, from incident personnel at a mass casualty scene, one or more physiological characteristics taken for each of a plurality of casualties and assigning a coded value for each based on the assessment;
 inputting the coded values into the computer system;
 establishing a severity score for each of the plurality of casualties by summing the coded values;
 receiving information indicative of medical transport resources available for the plurality of victims;
 inputting the information indicative of medical transport resources available into the computer system;
 assigning a survival probability to each severity score based upon at least one characteristic of a respective casualty or of an incident responsible for the casualty; and
 determining an order of transport for treatment for each of the plurality of casualties through analytical or mathematical programming techniques, wherein the programming techniques mathematically factor the severity scores, time periods of treatment delay resulting from constrained resources available for care of the plurality of casualties, the survival probabilities, and deterioration rates applied to the severity scores due to the time periods of treatment delay.

30. The computer readable medium of claim 29, wherein the method further comprises the step of calculating a number of expected survivors of the mass casualty incident through the analytical or mathematical programming techniques.

31. A computer readable medium that stores a program for performing a triage method for determining an order of transport from a mass casualty incident that maximizes the number of survivors of the mass casualty incident, the program comprising:
 means for receiving, from incident personnel at a mass casualty scene, a casualty severity score for each of a plurality of victims at the mass casualty scene;
 means for receiving information indicative of medical transport resources available for the plurality of victims at the mass casualty scene; and
 means for determining an order of transport for treatment for each of the plurality of victims, wherein the determination mathematically factors the casualty severity scores and the medical transport resources available.

32. A computer readable medium that stores a program for performing a triage method for determining an order of transport from a mass casualty incident that maximizes the number of survivors of the mass casualty incident, the program comprising:
 means for receiving, from incident personnel at a mass casualty scene, a casualty severity score for each of a plurality of casualties at the mass casualty scene;
 means for receiving information indicative of medical transport resources available for the plurality of victims at the mass casualty scene; and
 means for determining an order of transport for treatment for each of the plurality of victims, wherein the determination mathematically factors the medical transport resources available for the plurality of victims, the casualty severity scores, and casualty severity score deterioration rates resulting from time periods of treatment delay.

33. A computer readable medium that stores a program for performing a triage method for determining an order of transport from a mass casualty incident that maximizes the number of survivors of the mass casualty incident, the program comprising:
 means for receiving coded values, from incident personnel at a mass casualty scene, for one or more physiological characteristics taken for each of a plurality of victims at the mass casualty scene;
 means for receiving information indicative of medical transport resources available for the plurality of victims;
 means for establishing a casualty severity score for each of the plurality of victims using the coded values; and
 means for determining an order of transport for treatment for each of the plurality of victims, wherein the determination mathematically factors the medical transport resources available for caro of the plurality of victims and the casualty severity scores.

34. A computer readable medium that stores a program for performing a triage method for determining an order of treatment, or transport for treatment, for casualties of a mass casualty incident that maximizes the number of survivors of the mass casualty incident, the program comprising:
 means for receiving, from incident personnel at a mass casualty scene, one or more physiological characteristics taken for each of a plurality of casualties at the mass casualty scene and assigning a coded value for each based on the assessment;
 means for establishing a severity score for each of the plurality of casualties by summing the coded values;
 means for assigning a survival probability to each severity score based upon at least one characteristic of a respective casualty or of an incident responsible for the casualty;
 means for receiving information indicative of medical transport resources available for the plurality of casualties at the mass casualty scene; and
 means for determining an order of treatment, or transport for treatment, for each of the plurality of casualties through analytical or mathematical programming techniques, wherein the programming techniques mathematically factor the severity scores, the information indicative of medical transport resources available, time periods of treatment delay resulting from constrained resources available for care of the plurality of casualties, the survival probabilities, and deterioration rates applied to the severity scores due to the time periods of treatment delay.

35. The computer readable medium of claim 34, wherein the program comprises means for calculating a number of expected survivors of the mass casualty incident through the analytical or mathematical programming techniques.

36. A system for performing a triage method for determining an order of transport from a mass casualty incident that maximizes the number of survivors of the mass casualty incident, the system comprising:
 one or more portable computing devices for:
  receiving and inputting a casualty severity score for each of a plurality of victims of the mass casualty incident, the casualty severity score based on victim physiological characteristics;
  receiving and inputting information indicative of medical transport resources available for the plurality of victims of the mass casualty incident; and
 a computer processing unit at a central processing location for:

receiving the casualty severity scores for each of the plurality of victims, and the information indicative of medical transport resources available for the plurality of victims, as transmitted from the one or more portable computing devices; and determining an order of transport for treatment for each of the plurality of victims, wherein the determination mathematically factors the casualty severity scores and the medical transport resources available.

37. The system of claim 36, wherein the computer processing unit receives the casualty severity score for each of the plurality of victims via radio communication.

38. The system of claim 36, wherein the computer processing unit communicates the order of transport for treatment for each of the plurality of victims to the one or more portable computing devices for display thereon and use during an ordering of the victims at a scene of the mass casualty incident for transport from the scene of the mass casualty incident.

39. The system of claim 36, wherein determining an order of transport for treatment employs a score-based mathematical algorithm for resource-constrained triage that factors victim deterioration-with-time rates for each casualty severity score based upon an amount of time a victim awaits treatment.

40. The system of claim 39, wherein the victim deterioration-with-time rates are determined through consideration of factors selected from the group consisting of an availability of state-of-the-art, or lesser levels of treatment; a cause of a casualty incident; a type of anatomic injury incurred by the victim; an age of the victim; treatment available at the incident scene; treatment available at other facilities; distances to the other facilities; and facilities or equipment available for performance of casualty management.

41. The system of claim 36, wherein determining an order of transport for treatment employs a score-based mathematical algorithm for resource-constrained triage that factors one or more of a casualty severity score deterioration rate resulting from time periods of treatment delay, a type of trauma experienced by each casualty, a classification of each casualty, and a type of care center appropriate for and available to each casualty.

42. A triage method for determining an order of transport from a mass casualty incident that maximizes the number of survivors of the mass casualty incident, the method comprising the steps of:

assessing one or more physiological characteristics of each of a plurality of casualties at the mass casualty scene, by incident personnel at the mass casualty scene, and receiving from the incident personnel, or separately assigning, a coded value for each of the one or more physiological characteristics;

receiving from the incident personnel, or separately establishing, a casualty severity score for each of the plurality of casualties at the mass casualty scene using the coded value(s);

inputting each casualty severity score into a computer;

receiving from the incident personnel, or separately assigning, a survival probability to each casualty severity score based upon at least one characteristic of the respective casualty or of an incident responsible for the casualty;

inputting the survival probability for each casualty severity score into a computer;

establishing casualty severity score deterioration-with-time rates based upon at least one characteristic of an availability of state-of-the-art, or lesser levels of treatment; a cause of the casualty incident; a type of anatomic injury incurred by the casualty; an age of the casualty; treatment available at the mass casualty scene; treatment available at other facilities; distances to the other facilities; and facilities or equipment available for performance of casualty management;

inputting the casualty severity score deterioration-with-time rates into a computer;

receiving information indicative of medical transport resources available for the plurality of casualties;

determining by a computer implemented decision logic an order of transport for treatment for each of the plurality of casualties through analytical or mathematical programming techniques, wherein the programming techniques mathematically consider the casualty severity scores, the survival probabilities, the time periods of treatment delay resulting from constrained medical transport resources available for care-ef the plurality of casualties, and the casualty severity score deterioration-with-time rates applied to the severity scores due to the time periods of treatment delay;

communicating the order of transport for treatment to incident personnel; and ordering the plurality of casualties at the mass casualty scene for transport from the mass casualty scene in accordance with the order of transport for treatment determined.

* * * * *